(12) United States Patent
Lipton et al.

(10) Patent No.: US 6,780,838 B2
(45) Date of Patent: Aug. 24, 2004

(54) COMPOUNDS FOR TREATING FUNGAL PATHOLOGIES OF THE ORAL CAVITY

(75) Inventors: James M. Lipton, Woodland Hills, CA (US); Anna P Catania, Milan (IT)

(73) Assignee: Zengen, Inc., Woodland Hills, CA (US)

( * ) Notice: Subject to any disclaimer, the term of this patent is extended or adjusted under 35 U.S.C. 154(b) by 0 days.

(21) Appl. No.: 09/774,282

(22) Filed: Jan. 29, 2001

(65) Prior Publication Data

US 2002/0146374 A1 Oct. 10, 2002

(51) Int. Cl.$^7$ .................. A01N 37/18; A01N 25/34; A61K 38/00; A61K 9/00; C07K 14/00
(52) U.S. Cl. ..................... 514/2; 530/300; 424/400; 424/408
(58) Field of Search ................. 424/400, 408; 514/2; 530/300

(56) References Cited

U.S. PATENT DOCUMENTS

| | | | |
|---|---|---|---|
| 5,028,592 | A | 7/1991 | Lipton |
| 5,157,023 | A | 10/1992 | Lipton |
| 5,739,111 | A | 4/1998 | Mahe |
| 6,001,812 | A | 12/1999 | Mahe |
| 2002/0137685 | A1 * | 9/2002 | Catania et al. |

FOREIGN PATENT DOCUMENTS

| | | |
|---|---|---|
| EP | 0972 522 A1 | 1/2000 |
| FR | 2784028 | 4/2000 |
| WO | WO 93/01211 | 1/1993 |
| WO | WO/97/10838 | 3/1997 |
| WO | WO/99/58101 | 11/1999 |
| WO | PCT/US00/07846 | 3/2000 |
| WO | WO00/42856 | 7/2000 |

OTHER PUBLICATIONS

Csato, M. et al., "Enhancement of *Candida albicans* killing of separated human epidermal cells by alpha–melanocyte stimulating hormone." Br. J. Dermatol. 1989, vol. 121. No. 1, pp. 145–147, see entire document.

Chow, C.K.W. et al., "Efficacy of antifungal agents in tissue conditioners in treating candidiasis." Gerodontology. 1999, vol. 16, No. 2, pp. 110–118, see entire document.

Cutuli, M. et al., "Antimicrobial effects of alpha–MSH peptides." J. Leukoeyte Biology 2000, vol. 67, No. 2 pp. 233–239.

Marchetti, O. et al., "Potent synergism of the combination of fluconazole and cyclosporin in *Candida albicans*." Antimicrobial Agents and Chemotherapy. Sep. 2000, vol. 44, No. 9, pp. 2373–2381.

Odds, F.C. et al., "Improved method for estimation of azole antifungal inhibitory concentrations against Candida species, based on azole/antibiotic interactions." J. Med. Vet. Mycol. 1986, vol. 24, pp. 305–311.

Airaghi, L., et al., "Elevated concentrations of plasma α–MSH are associated with reduced disease progression in HIV–infected patients," J. Lab. Clin. Med. 133(3) 309–315 (1999).

Airaghi L, Lettino M, Manfredi MG, Lipton JM, Catania A. Endogenous cytokine antagonists during myocardial ischemica and thrombolytic therapy. Am. Heart J. 130: 204–211, 1995.

Airaghi L. Garofalo L. Cutuli MG. Delgado R. Carlin A. Demitri MT. Badalamenti S. Graziani G. Lipton JM. Catania A. Plasma concentrations of α–melanocyte–stimulating hormone are elevated in patients on chronic haemodialysis. Nephrology Dialysis Transplantation 15:1212–1216, 2000.

Baker, M., et al., "The Relationship between Interleukin–6 and Simplex Virus Type–1: Implications for Behavior and Immunopathology," *Brain Behav. Immun.* 13(3):201–11 (1999).

Baker, et al., "Principles of Ambulatory Medicine," *Williams and Wilkins* (*1982*).

Barcellini, W., et al., "Inhibitory Influences of α–MSH peptides on HIV–1 expression in Monocytic cells," 12$^{th}$ World AIDS Conference Geneva, Abstract No. 60685, Jun. 28–Jul. 3, 1998.

(List continued on next page.)

Primary Examiner—Robert Landsman
(74) Attorney, Agent, or Firm—Michael J. Wise; Perkins Coie LLP (57) ABSTRACT

The broadest aspect of the invention is a composition and method of treatment of fungal pathologies of the oral cavity or fungal growth on the surface of dentures. A preferred embodiment of the is a pharmacologically effective amount of a peptide selected from the group of peptides with a C-terminal sequence consisting of KPV(SEQ ID NO: 1), HFRWGKPV(SEQ ID NO: 3), and SYSMEHFRWGKPV (SEQ ID NO: 4) in combination with a therapeutically effective amount of a fungicide selected from the group consisting of: itraconazole, econazole, ketoconazole, miconazole, imconazole and fluconazole. Another embodiment of the invention is a method for treating fungal pathologies of the oral cavity and dentures by application of a pharmacologically effective amount of a peptide selected from the group of peptides with a C-terminal sequence consisting of KPV (SEQ ID NO: 1), HFRWGKPV (SEQ ID NO: 3), and SYSMEHFRWGKPV (SEQ ID NO: 4) in combination with a therapeutically effective amount of a fungicide selected from the group consisting of: itraconazole, econazole, ketoconazole, miconazole and fluconazole. In yet another embodiment of the invention these peptides are used in combination with a therapeutically effective amount of gram positive and/or gram negative antibiotics.

23 Claims, 7 Drawing Sheets

OTHER PUBLICATIONS

Barcellini W, La Maestra L, Clerici G, Garofalo L, Brini AT, Lipton JM, Catania A. α–MSH peptides inhibit HIV–1 expression in chronically infected promonocytic U1 cells and in acutely infected monocytes. Journal of Leukocyte Biology 68:693–699, 2000.

Bhattacharya A., et al., "Effect of Cyclic AMP on RNA and Protein Synthesis in *Candida albicans,*" *Biochem, Biophysics. Res. Commun.,* 77: 1438–44 (1977).

Bickers, D., Sun–Induced Disorders, *Emergency Medicine Clinicis of North America,* 3(4):659–663, 660 (1985).

Capsoni, F., et al., "Effect of Corticosteroids on Neutrophil Function: Inhibition of Antibody–dependent Cell–Mediated Cytotoxicity (ADCC)," *J. Immunolpharmacol,* 5 217–30 (1983).

Cartledge, J.D., et al., "Clinically Significant Azole–Cross–Resistance in Candida Isolates from HIV–Positive Patients with Oral Candidosis," *AIDS* 11:1839–44 (1997).

Catania, A., et al., "α–Melanocyte Stimulating Hormone in the Modulation of Host Reactions," *Endocr. Rev.* 14, 564–576 (1993).

Catania, A., et al., "Melanocortin Peptides Inhibit Production of Proinflammatory Cytokines in Blood of HIV–Infected Patients," *Peptides,* 19(6): 1099–1104 (1998).

Catania, A., et al., "The Neuropeptide α–MSH in HIV Infection and Other Conditions in Humans,"*Ann. N.Y. Acad. Sci.* 840: 848–856 (1988).

Catania, A.; et. al., "The Neuropeptide α–MSH has Specific Receptors on Neutrophils and Reduces Chemotaxis in Vitro," *Peptides* 17, 675–679 (1996).

Catania A, Airaghi L, Lipton JM. α–MSH in normal human physiology and disease states. Trends Endocrinol. Metab. 11:304–308, 2000.

Catania A, Delgado R, Airaghi L, Cutuli M, Garofalo L, Carlin A, Demitri MT, Lipton JM. α–MSH in systemic inflammation: central and peripheral actions. Annals of the New York Academy of Sciences, 885:183–187, 1999.

Catania A, Grazia M, Manfredia MG, Airaghi L, Ceriani G, Gandino A, Lipton JM. Cytokine antagonists in infectious and inflammatory disorders. Annals of the New York Academy of Sciences 741: 149–161, 1994.

Catania A. Lipton JM. α–melanocyte–stimulating horomone peptides in host responses: from basic evidence to human research. Annals of the New York Academy of Sciences 680: 412–423, 1993.

Catania A, Cutuli M, Garofalo L, Airaghi L, Valenza F, Lipton JM, Gattinoni L. Plasma concentrations and anti–L–cytokine effects of αmelanocyte stimulating hormone in septic patients. Crit. Care Med. 28: 1403–1407, 2000.

Catania A, Airaghi L, Motta P, Manfredi MG, Annoni G, Pettenati C, Brambilla F and Lipton JM. Cytokine antagonists in aged subjects and their relation with cellular immunity. Journal of Gerontology: Biological Sciences 52A: B93–97, 1997.

Catania A, Manfredi MG, Airaghi L, Vivirito MC, Capetti A, Milazzo, F, Lipton JM and Zanussi C. Plasma concentration of cytokine antagonists in patients with HIV infection. Neuroimmunomodulation 1: 42–49, 1994.

Catania A, Airaghi L, Manfredi MG, Vivirito MC, Milazzo F, Lipton JM, Zanussi C: Proopiomelanocortin–derived peptides and cytokines: relations in patients with acquired immunodeficiency syndrome. Clinical Immunology and Immunopathology 66: 73–79, 1993.

Cavello, J. and Deleo, V., Sunburn, *Dermatologic Clinics,* 4(2): 181–187, 181 (1986).

Ceriani, G., et. al., "Central Neurogenic Antiinflammatory Action of α–MSH: Modulation of Peripheral Inflammation Induced by Cytokines and other Mediators of Inflammation," *Neuroendocrinology,* 59:138–143 (1994).

Ceriani G, Diaz J, Murphree S, Catania A, Lipton JM. The neuropeptide alpha–melanocyte–stimulating hormone inhibits experimental arthritis in rats. Neuroimmunomodulation 1:28–32, 1994.

Chiao H, Foster S, Thomas R, Lipton J, and Star RA. α–MSH reduces endotoxin–induced liver inflammation. J. Clin. Invest. 97:2038–2044, 1996.

Csato, M. et al., "Enhancement of Candida albicans killing activity of separted human epidermal cells by alpha–melanocyte stimulating hormone," British Journal of Dermatology, 121(1) 145–147 (1989).

Cutuli, M. et al., "Antimicrobial effects of α–MSH peptides," Journal of Leukocyte Biology 67:233–239 (2000).

Deeter, L.B., et al., Antipyretic Properties of Centrally Administered α–MSH Fragments in the Rabbit, *Peptides* (, 1285–1288 (1989).

Delgado, R., et al., "Melanocortin peptides inhibit production of proinflammatory cytokines and nitric oxide by activated microglia," *Journal of Leukocyte Biology,* 63: 740–745 (1998).

Domk–Optiz, I., et al., "Stimulation of Macrophages by Endotoxin Results in the Reactivation of a Presistent Herpes Simplex Virus Infection," *Scand J. Immunol.* 32(2):69–75 (1990).

Eberle, A. and Schwyzer, R., Hormone–Receptor Interactions, *Clinical Endocrinology* 5, Suppl., 41s–48s (1976).

Eberle, A.N., The Malanotrophins, *Karger, Basel, Switzerland* (1988).

Fauci, A.S., "Host Factors in the Pathogenesis of HIV–induced Disease," *Nature* 384: 529 (1996).

Fitzpatrick, et al., Acute Effects of Ultraviolet Radiation on the Skin: The Sunburn Reaction, *Dermatology in General Medicine,* 4th Edition, 1651–1655, 1651 (1993).

Fitzpatrick, et al., "Color Atlas and Synopsis of Clinical Dermatology," (1983).

Foster, J. Sunburn, *eMedicine—Online Medical Reference Textbook,* (last modified May 1, 2000), <http://emedicine.com/emerg/topic798.htm.

Fox, J. A., et al., "Immunoreactive α–Melanocyte Stimulating Hormone, Its Distribution in the Gastrointestinal Tract of Intact and Hypophysectomized Rats," *Life. Sci.* 28, 2127–2132 (1981).

Galimberti D, Baron PL, Meda L, Prat E, Scarpini E, Delgado R, Catania A, Lipton JM, Scarlato G. α–MSH peptides inhibit production of nitric oxide and tumor necrosis factor–α by microglial cells activated with β–amyloid and interferon γ. Biochemical Biophysical Research Communications 263: 251–256,1999.

Gow, N.A., "Germ Tube Growth of *Candida albicans,*" *Curr. Topics Med. Myco.* 8, 43–55 (1997).

Hart, D.A., et al., "*Staphylococcus Aureus* Strains Differ in Their in Vitro Responsiveness to Human Urokinase: Evidence that Methicillin–Resistant Strains are Predominantly Nonresponsive to the Growth–Enhancing Effects of Urokinase," *Can. J. Microbiol.* 42: 1024–31 (1966).

"Harry's Comseticology", *Chemical Publishing, 7th ed.* (1982).

Hiltz, M. E., et al., "Anti–inflmmatory Activity of a COOH–terminal Fragment of the Neuropeptide α–MSH," *FASEB J.* 3, 2282–2284 (1989).

Hiltz, M.E., "Anti–inflammatory Activity of α–MSH (11–13) Analogs: Influences of Alterations in Stereochemistry," *Peptides* 12, 767–71 (1991).

Hiltz, M.E., et al., "Alpha–MSH Peptides Inhibit Acute Inflammation and Contact Sensitivity," *Peptides,* 11:979–982 (1990).

Hiltz, M.E., et al., "α–MSH Peptides Inhibits Acute Inflammation Induced in Mice by rIL–1β, rIL–6, rTNF–α and endogenous pyrogen but not that cause by LTB4, PAF and rIL–8," *Cytokine* 4(4):320–328 (1992).

Holdeman, M., et al., "Antipyretic Activity of a Potent α–MSH Analog," *Peptides* 6, 273–5 (1985).

Huh S–K, Lipton JM and Batjer HH. The protective effects of α–melanocyte stimulating hormone on canine brainstem ischemia. Neurosurgery 40:132–139, 1997.

Ichiyama T, Sakai T, Catania A, Barsh GS, Furukawa S, Lipton JM. Systemically administered α–melanocyte–stimulating hormone peptides inhibit NF–κB activation in experimental brain inflammation. Brain Research 836: 31–37, 1999.

Ichiyama T, Zhao H. Catania A, Furukawa S, Lipton JM. α–melanocyte–stimulating hormone inhibits NF–κB activation and IαBκ degradation in human glioma cells and in experimental brain inflammation. Experimental Neurology 157:359–365, 1999.

Ichiyama T, Campbell IL, Furukawa S, Catania A, Lipton JM. Autocrine α–melanocyte–stimulating hormone inhibits NF–κB activation in human glioma cells. Journal of Neuroscience Research 58:684–689, 1999.

Ichiyama T. Okada K, Campbell IL, Furukawa S, Lipton JM. NF–κB activation is inhibited in human pulmonary epithelial cells transfected with α–melanocyte–stimulating hormone vector. Peptides 21: 1473–1477, 2000.

Ichiyama T, Sakai T, Catania A, Barsh GS, Furukawa S, Lipton JM. Inhibition of peripheral NF–78 B activation by central action of α–melanocyte–stimulating hormone. Journal of Neuroimmunology 99: 211–217, 1999.

Lichtensteiger, W., and Monnet, F., "Differential Response of Dopamine Neurons to α–Melanotropin and Analogues in Relation to Their Endocrine and Behavioral Potency," *Life Sci.* 25:2079–2087 (1987).

Lipton, J.M., et al., "Anti–inflmmatory Effects of the Neuropeptide α–MSH in Acute Chronic and Systemic inflammation," *Ann. N.Y. Acad. Sci.* 741, 137–148 (1994).

Lipton, J.M., et al., "Anti–inflammatory Actions of the Neuroimmunomodulator α–MSH," *Immunol. Today* 18, 140–145 (1997).

Lipton, J.M., "Neuropeptide α–Melanocyte–Stimulating Hormone in Control of Fever, the Acute Phase Response, and Inflammation," *Neuroimmune Networks: Physiology and Diseases,* (Alan R. Liss, Inc. 1989), pp. 243–250.

Lipton, J.M., Modulation of Host Defense by the Neuropeptide α–MSH,*The Yale Journal of Biology and Medicine* 63: 173–182 (1990).

Lipton JM, Catania A, Ichiyama T. Marshalling the anti–inflammatory influence of the neuroimmunomodulator α–MSH. News Physiol. Sci, 15: 192–195, 2000.

Lipton JM, Catania A. The neuropeptide α–MSH: a modulator of host reactions. Seminars in Clinical Immunology 10:25–29, 1995.

Luger, T.A., et al., "Production of Immunosuppressing Melanotropins by Human Keratinocytes," *Ann. N.Y. Acad. Sci.* 680: 567–570 (1993).

Lyson, K., et al., "Binding of Anti–Inflammatory α–Melanocyte–Stimulating Hormone Peptides and Proinflammatory Cytokines to Receptors on Melanoma Cells," *Neuroimmunomodulation,* 1:121–126 (1994).

Macaluso, A., et al., "Antiinflammatory Influences of α–MSH molecules: Central Neurogenic and Peripheral Actions," *The Journal of Neuroscience,* 14(4): 2377–2382 (1994).

Mayhall, Ten Home Remedies for Sunburn, *Seasonal Health,* (Jul. 14, 2000). <http://drkoop.com/wellness/seasonal/summer/sunburn.html>.

Mugridge, K.G., et al., "α–Melanocyte–Stimulating Hormone reduces interleukin–1β effects on rat stomach preparations possibly through interference with type I receptor," *European Journal of Pharmacology,* 197: 151–155 (1991).

Noisakran S., e. al. "Lymphocytes Delay Kinetics of HSV–1 Reactivation from in vitro Explants of Latent Infected Trigeminal Ganglia," *J. Neuroimmunol.* 95(1–2):126–35 (1999).

Patel, A., et al., "Herpes Simplex Type 1 Induction of Persistent NF–κB Nuclear Translocation Increases the Efficiencty of Virus Replication," *Virology* 247(2):212–22 (1998).

Potts, Sunlight, Sunburn, and Sunscreens, *Postgrad. med.* 87:52–61 (1990).

Rajora, N., et al., "α–MSH Modulates Local and Circulating tumor Necrosis Factor α in Experimental Brain Inflammation" *J. Neuroosci,* 17, 2181–2186 (1997).

Rajora, N., et al., "α–MSH Production Receptors and Influence on Neopterin, in a Human Monocyte/macrophage Cell Line," *J. Leukoc. Biol. 59,* 248–253 (1996).

Rajora N, Boccoli G, Catania A and Lipton JM. α–MSH modulates experimental inflammatory bowel disease. Peptides 18:381–385, 1997.

Remington's Pharmaceutical Sciences, *Mack Publishing Co., 18$^{th}$ ed.* (1990).

Richards, D.B., et al., "Effect of a–MSH (11–13) (lysine–proline–valine) on Fever in the Rabbit," *Peptides* 5, 815–817 (1984).

*Robbins Pathologic Basis of Disease 5$^{th}$ ed.,* Saunders Co., Philadelphia (1994) p. 335–337, 354–355, 1008, 1037–1038.

Ryan, et al., "Inflammation," *a Scope Publication, The Upjohn Company,* (1977).

Star, R.A., et. al., "Evidence of Autocrine Modulation of Macrophage Nitric Oxide Synthase by α–MSH," *Proc. Nat'l. Acad. Sci. (USA)* 92, 8015–8020 (1995).

Stevens, D.L., "Could Nonsteriodal Anti–inflammatory Drugs (NSAIDs) Enhance Progression of Bacterial Infections to Toxic Shock Syndrome?," *Clin. Infect. Dis.* 21, 977–80 (1997).

Szalay, K.S., et al., "Structure–activity studies with ACTH/α–MSH fragments on corticosteroid secretion of isolated zona glomerulos and fasciculata cells," *Regulator Peptides,* 11: 187–192 (1985).

Taherzadeh S, Sharma S, Chhajlani V, Gantz I, Rajora N, Demitri MT, Kelly L, Zhao H, Catania A, Lipton JM. α–MSH and its receptors in regulation of tumor necrosis factor–α production by human monocyte/macrophages. Am. J. Physiol. 276:R1289–R1294, 1999.

Thody, A.J., et al., "MSH Peptides are Present in Mammalian Skin," *Peptides* 4, 813–815 (1983).

Uehara, Y., et al., "Carboxyl–terminal tripeptide of α–Melanocyte–Stimulating Hormone anagonizes interluekin–1–induced anorexia," *European Journal of Pharmacology*, 220: 119–122 (1992).

van Nispen, J.W. and Greven, H.M., "Structure–Activity Relationships of Peptides Derived From ACTH, β–LPH and MSH With Regard To Avoidance Behavior in Rats," *Pharmac. Ther.* 16: 67–102 (1982).

Walev, I., et al., "Enhancement by TNF–alpah of Reactivation and Replication of Latent Herpes Simplex Virus from Trigeminal Ganglia of Mice," *Arch Virol.* 140(6):987–92 (1995).

Watanabe T, Hiltz, ME, Catania A, Lipton JM. Inhibition of IL–1β–induced peripheral inflammation by peripheral and central administration of analogs of the neuropeptide α–MSH. Brain Research Bulletin 32: 311–314, 1993.

Wenzel, R.P. and Pfaller, M.A., "Candida Species: Emerging Hospital Bloodstream Pathogens," *Infect. Control. Hosp. Epidemiol.* 12: 523–4 (1991).

Wong, K.Y., et al., "A Potential Mechanism of Local Anti–inflammatory Action of Alpha–Melanocyte–Stimulating Hormone within the Brain: Modulation of Tumor Necrosis Factor–Alpha Production by Human Astrocytic Cells," *Neuroimmunomodulation*, 4:37–41 (1997).

"Vaginitis," National Institute of Child Health and Human Development—Publications On–line (last modified Jan. 12, 2000).<www.nichd.nih.gov/publications/pubs/vagtoc.html>.

"Tampons and Asbestos, Dioxins, & Toxic Shock Syndrome," FDA Center for Devices and Radiological Health (Jul. 23, 1999), <http://www.fda/gov/cdrh/ocd/tamponsabs.html>.

Khurshid, M.A., et al., :Staphylococcus aureus with Reduced Susceptibility to Vancomycin—Illinois, 1999, *Morbidity and Mortality Weekly Report,* 48(51): 1165–1167 (2000), <http://www.cdc.gov/epo/mmwr/preview/mmwrhtml/mm4851a1.html>.

"Women's Health, Urinary Tract Infections: A Patient's Guide to Treatment," *AMA Health Insight, On–Line Health Information for Everyone* (last updated Oct 30, 1998), <http://www.ama–assn.org/insight/h_focus/wom_hlth/uti/uti.html>.

Getting, et al., POMC Gene–Derived Peptides Activate Melanocortin Type 3 Receptor on Murine Macrophages, Suppress Cytokine Release, and Inhibit Neutrophil Migration in Acute Experimental Inflammation, J. Immunol., vol. 162, No. 12, pgs. 7446–7453, (1999).

Harris, et al., Alpha–melanocyte stimulating hormone (a–MSH) and melanin–concentrating hormone (MCH) stimulate phagocytosis by head kidney leucocytes of rainbow trout (*Oncorhynchus mykiss*) in vitro, Fish & Shellfish Immunol., vol. 8, 8:631–638 (1998).

Huang, et al., Role of central melanocortins in endotoxin–induced anorexia, Am. J. Physio (Regulatory, Integrative & Comparative Physiology, vol. 276, No. 3, pgs. R864–R871 (1999).

Lipton, et al., Mechanisms of antiinflammatory action of the neuro immunonomodulatory peptide alpha–MSH, Annals of the N.Y. Acad. Sci., vol. 840, pgs. 373–380 (1998).

Weiss, et al., Corticotropin–peptide regulation of intracellular cyclic–AMP production in cortical neurons in primary culture, J. Neurochem. vol. 45, No. 3, pgs. 869–874 (1985).

* cited by examiner

SEQUENCE LISTING

```
<160> NUMBER OF SEQ ID NOS: 10

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term may or may not be acetylated
<220> FEATURE:
<223> OTHER INFORMATION: c-term may or may not be amidated

<400> SEQUENCE: 1

Lys Pro Val
 1

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term may or may not be acetylated
<220> FEATURE:
<223> OTHER INFORMATION: c-term may or may not be amidated

<400> SEQUENCE: 2

Met Glu His Phe Arg Trp Gly
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term may or may not be acetylated
<220> FEATURE:
<223> OTHER INFORMATION: c-term may or may not be amidated

<400> SEQUENCE: 3

His Phe Arg Trp Gly Lys Pro Val
 1               5
```

```
<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term may or may not be acetylated
<220> FEATURE:
<223> OTHER INFORMATION: c-term may or may not be amidated

<400> SEQUENCE: 4

Ser Tyr Ser Met Glu His Phe Arg Trp Gly Lys Pro Val
 1               5                  10

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Tyr Ser Met Glu His Phe Arg Trp Gly Lys Pro Val Gly Lys Lys
 1               5                  10                  15

Arg Arg Pro Val Leu Val Tyr Pro Ala Gly Glu Asp Asp Glu Ala Ser
            20                  25                  30

Glu Ala Phe Pro Leu Glu Phe
        35

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Pro Val Leu Val Tyr Pro Ala Gly Glu Asp Asp Glu Ala Ser Glu
 1               5                  10                  15

Ala Phe Pro Leu Glu Phe
            20

<210> SEQ ID NO 7

<400> SEQUENCE: 7

000

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of modifications and preferred embodiments

<400> SEQUENCE: 8

Cys Lys Pro Val
 1
```

-continued

```
<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Nle
<220> FEATURE:
<221> NAME/KEY: MOD_RES
<222> LOCATION: (7)
<223> OTHER INFORMATION: D-Phe

<400> SEQUENCE: 9

Ser Tyr Ser Xaa Glu His Phe Arg Trp Gly Lys Pro Val
     1               5                  10

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Lys
<220> FEATURE:
<223> OTHER INFORMATION: c-term amidation

<400> SEQUENCE: 10

Lys Pro Val
     1
```

COMPOUNDS FOR TREATING FUNGAL PATHOLOGIES OF THE ORAL CAVITY

BACKGROUND OF THE INVENTION

This invention relates to the field of pathologies of the oral cavity caused by fungi.

One of the most common and stubborn infections of the mouth and throat is Candidiasis. Thrush or acute candidiasis is caused by extensive candidal invasion of the oral mucosal epithelium. Thrush presents as creamy, yellow tufts which can be readily wiped off with a swab to expose a red and inflamed area of epithelium. The cottony tufts are the result of extensive infiltration of candidal hyphae into the mucosal epithelium.

Although thrush is most common in infants, it also occurs in adults that are immunocompromised, undergoing broad spectrum antibiotic treatment, undergoing corticosteroid treatment, diabetics and anemics. In adult patients, particularly immunosuppresed patients, thrush is treated with large amounts of azole compounds such as miconazole, itraconazole, econazole, ketoconazole or fluconazole. Among thrush patients not already undergoing broad-spectrum antibiotic treatment, broad-spectrum antibiotics are frequently prescribed in combination with fungicide therapy to avoid or treat any secondary bacterial infections. Infants are usually treated with fungicidal suspensions if the infection does not spontaneously clear.

Chronic candidiasis is both far more common and far more difficult to treat than thrush. Candidiasis is characterized by less extensive innervation of the epithelium by the Candidal hyphae than thrush.

Candidal proliferation on denture surfaces is a common, chronic, but minor form of candidiasis. Inflammation of the epithelium under dentures, denture stomatitis, may be caused by the proliferation of *C. albicans* in the interface between the denture-bearing mucous membrane and the denture surface. The lower denture-bearing area is typically freely exposed to saliva, and consequently denture stomatitis is rarely seen in this site. However, a close-fitting upper denture creates a microenvironment cut-off from any protective effects of saliva. When *C. albicans* proliferates under a denture, it is held in prolonged contact with the mucous membrane and presumably acts as an irritant.

Denture stomatitis is considered a common cause of inflammation of the epithelium near the corners of the mouth, angular stomatitis, among ambulatory patients. Typical treatment requires vigorous use of topical oral nystatin or amphotericin B to resolve denture stomatitis and associated angular stomatitis. During treatment, the dentures must be worn as little as possible to allow the drug to the reach affected area, thus, inconveniencing suffering denture wearers.

Candidal leukoplakia is a less common type of chronic candidiasis, appearing as a thick keratizined lesion on or about the tongue. Microscopically, a candidal leukoplia plaque consists of a thick layer parakeratinized epithelium invaded by candidal hyphae. These keratinized plaques of chronic candidiasis are tough, adherent, and often irregular in thickness, persistent, and therefore, unlike the soft friable plaques of thrush. Common sites are the commissures of the tongue and cheeks. Treatment of candidal leuloplakia infections are difficult since the intracellular growth of the candida makes it less accessible to antifungal drugs. Absent treatment, these leukoplakias often cover large areas of the mouth and tongue, making eating painful and causing significant social anxiety among the afflicted.

A number of rare forms of chronic mucocutaneous candidiasis appear associated with various immune disorders. Familial chronic mucocutaneous candiasis is a rare, recessive, immune disorder which confers a tendency to develop chronic, leukoplakia-like plaques. Diffuse chronic mucocutaneous candidiasis is associated with susceptibility to bacterial infections, particularly of the respiratory tract, and other fungal infections. Its lesions may extend down the pharynx or larynx and when affecting the mouth and lips, can be severely disfiguring. Candida endocrinopathy syndrome appears to be transmitted as an autosomal recessive gene. The candidal infections tend to be mild and dermal lesions are rare. The main features are the associated endocrine deficiencies. Most common is hypoparathyroidism, but hypoadrenalism and almost any other type of endocrine deficiency can develop.

Treatment for all these candidal immune disorders are difficult. If the immunological defect can be identified, as is sometimes the case with diffuse chronic mucocutaneous candidiasis, treatment may be possible, but generally treatments are ineffective because they fail to address the underlying immunological disorder that allows the candida to flourish.

The foregoing discussion indicates that an effective fungicide against a wide range of candidal pathologies useful in immuno-compromised patients, children, and the elderly that can either be topically applied or systemically applied to treat the chronic candidal infections like candidal leukoplakia that is resistant to topical treatment would be a significant advance to the art. Such a fungicidal should preferably have low toxicity and even more preferably possess anti-inflammatory properties. Lastly, the fungicidal should also have minimal cross reactivity with other drugs so that it may be simultaneously prescribed with the complicated treatment regimens of the elderly and chronically ill-two groups likely to suffer candidiasis.

SUMMARY OF THE INVENTION

The invention includes a composition and method of treatment of fungal pathologies of the oral cavity or fungal growth on the surface of dentures. In a preferred embodiment of the invention a therapeutically effective amount of one or more peptides selected from the group of peptides with a C-terminal sequence consisting of KPV (SEQ ID NO: 1), HFRWGKPV (SEQ ID NO: 3), and SYSMEHFR-WGKPV (SEQ ID NO: 4) used in combination with a therapeutically effective amount of a fungicide selected from the group consisting of: itraconazole, econazole, ketoconazole, miconazole and fluconazole and dissolved into a carrier. More preferably still each peptide has the primary sequence of KPV (SEQ ID NO: 1) or VPK-Ac-CC-Ac-KPV (SEQ ID NO: 8)(Ac=Acetyl group). Pharmacologically effective concentrations may be as low as $10^{-12}$ M but may be as high $10^{-4}$ M. Pharmacologically effective concentration of these peptides may be incorporated into commercial formulations of creams, gels, mouthwashes, toothpastes, tablets, or atomized sprays.

In another preferred embodiment of the invention these peptides are topically or systemically applied to treat a candida infection of the oral cavity. In yet another embodiment of the invention these peptides are used in combination with a therapeutically effective amount of a gram positive or gram negative antibiotic to prevent or treat secondary bacterial infections of the oral cavity or on the surface of dentures.

DETAILED DESCRIPTION OF THE INVENTION

α-MSH is a 13 amino acid (SEQ ID NO: 4), fungicidal peptide with the primary sequence SYSMEHFRWGKPV (SEQ ID NO: 4). In addition to its fungicidal properties it also anti-pyretic and anti-inflammatory. The C-terminal trimer, KPV (SEQ ID NO: 1). appears responsible for these properties. Lipton, J. M., Antipyretic and Anti-inflammatory Lys-Pro-Val (SEQ ID NO: 1) Compositions and Methods of Use, U.S. Pat. No. 5,028,592, issued Jul. 2, 1991;Lipton, J. M., Antipyretic and Anti-inflammatory Lys-Pro-Val (SEQ ID NO: 1) Compositions and Methods of Use, U.S. Pat. No. 5,157,023, issued Oct. 20, 1992; Catania, A., Lipton J. M., α-*Melanocyte Stimulating Hormone in the Modulation of Host Reactions, Endocr. Rev.* 14, 564–576 (1993); Lipton, J. M., Catania, A., *Anti-inflammatory Influence of the Neuroimmunomodulator α-MSH, Immunol. Today* 18, 140–145 (1997). herein incorporated by reference. All references are hereby incorporated by reference in their entirety. The core α-MSH sequence (4–10) (SEQ ID NO: 2) has learning, memory and behavioral effects but little antipyretic and anti-inflammatory activity. Lipton, J. M., Catania, A., *Anti-inflammatory Influence of the Neuroimmunomodulator α-MSH, immunol. Today* 18, 140–145 (1997). α-MSH, the α-MSH core and its tripeptide C-terminal have very low toxicity. Lipton, J. M., Catania, A., *Anti-inflammatory Influence of the Neuroimmunomodulator α-MSH, Immunol. Today* 18, 140–145 (1997).

α-MSH is produced by the post translational processing of propriomelanocortin and shares the 1–13 primary sequence with adrenocortitrophic hormone (ACTH). Eberle, A. N., *The Melanotropins*, Karger, Basel, Switzerland (1988). It is secreted by a wide variety of cell types, including pituitary cells, monocytes, melanocytes, keratinocytes, epidermal cells and the epithelial cells of mucous membranes. Lipton, J. M., Catania, A., *Anti-inflammatory Influence of the Neuroimmunomodulator α-MSH, Immunol. Today* 18, 140–145 (1997); see also Catania et al., unpublished.

α-MSH reduces inflammation and fever by modulating the inflammatory cascade locally and systemically. Rajora, N., Ceriani, G., Catania, A., Star, R. A., Murphy, M. T., Lipton, J. M., α-*MSH Production Receptors and Influence of Neopterin in a Human Monocyte/macrophage Cell Line, H.Leukoc. Biol.* 59, 248–253 (1996); Star, R. A., Rajora, N. Huang, J., Stock, R. C., Catania, A., Lipton, J. M., *Evidence of Autocrine Modulation of Macrophage Nitric Oxide Synthase by α-MSH, Proc. Natl. Acad. Sci.* 92, 8016–8020 (1995); Lipton, J. M., Ceriani, G., Macaluso, A., McCoy, D., Carnes, K., Biltz, J., Catania, A., *Anti-inflammatory Effects of the Neuropeotide α-MSH in Acute, Chronic and Systemic Inflammation, Ann. N.Y. Acad. Sci.* 741, 137–148 (1994); Rajora, N., Boccoli, G. Burns, D., Sharma, S., Catania, A., Lipton, J. M., α-*MSH Modulates Local Circulating Tumor Necrosis Factor A in Experimental Brain Inflammation, J. Neurosci*, 17, 2181–2186 (1997); Richards, D. B., Lipton, J. M. Effect of α-*MSH* (11–13) (*Lys-Pro-Val*) (*SEQ ID NO: 1*) *on Fever in Rabbits, Peptides* 5, 815–817 (1984); Hiltz, M. E., Lipton, J. M., *Anti-inflammatory Activity of a COOH-terminal Fragment of the Neuropeotide α-MSH*. FASEB J.3, 2282–2284 (1989).

The broadest aspect of the invention is a composition and method of treatment of fungal pathologies of the oral cavity or fungal growth on the surface of dentures. In a preferred embodiment of the invention a therapeutically effective amount of one or more peptides selected from the group of peptides with a C-terminal sequence consisting of KPV (SEQ ID NO: 1), HFRWGKPV (SEQ ID) NO: 3), and SYSMEHFRWGKPV (SEQ ID NO: 4) is incorporated into a carrier. More preferably still, each peptide has the primary sequence of KPV (SEQ ID NO: 1) or VPK-Ac-CC-Ac-KPV (SEQ ID NO: 8) (Ac=Acetyl group). Pharmacologically effective concentrations may be as low as $10^{-12}$ M but may be as high as $10^{-4}$ M. A preferred embodiment of the invention utilizes peptide concentrations of $10^{-12}$ M to $10^{-10}$ M. Pharmacologically effective concentrations of these peptides may be incorporated into commercial formulations of creams, gels, mouthwashes, toothpastes, tablets, or atomized sprays.

Formulations of creams and gels are well known in the art. Harry's Comseticology (Chemical Publishing, 7th ed. 1982); REMINGTON'S PHARMACEUTICAL SCIENCES (Mack Publishing Co., 18th ed. 1990).

Set forth below are examples of various formulations of the invention. As used below the term "Active ingredient" refers to one or more peptides selected from the group of peptides with a C-terminal sequence consisting of KPV (SEQ ID NO: 1), HRFWGKPV (SEQ ID NO: 3) and SYSMEHFRWGKPV (SEQ ID NO: 4). Preferably, the active ingredient is KPV (SEQ ID NO: 1) or VPK-Ac-CC-Ac-KPV (SEQ ID NO: 8).

An exemplary formulation of a gel based on the invention comprises:

| | |
|---|---|
| Propylene Glycol | 10.0 g |
| PEG-Glyceryl Cocoate | 10.0 g |
| di-α-Tocopherol | .02 g |
| Ascorbyl Palmitate | .10 g |
| Propyl Gallate | .002 g |

-continued

| | |
|---|---|
| Citric Acid, annhydr | .01 g |
| Isopropanol | 50.0 g |
| Hydroxypropyl Methyl Cellulose | 3.00 g |
| Water | 100 g |
| Active ingredient | $.2-.2*10^{-8}$ mg |

An exemplary formulation of a cream comprises:

| | |
|---|---|
| Glycerol | 5.0 g |
| Na$_2$-EDTA | .03 g |
| Glycerides | 10.0 g |
| Cetyl Alcohol | 1.0 g |
| Stearyl Alcohol | 1.0 g |
| Glycerol mono Stearate | 4.0 g |
| Cetereth | 2.0 g |
| di-α-tocopherol | .02 g |
| Water | 100.0 g |
| Active Ingredient | $.1-.1*10^{-8}$ mg |

Formulations for toothpastes, and mouthwashes are well known in the art. U.S. Pat. Nos. 4,719,100; 4,314,990 and 4,151,271. An exemplary formulation of a toothpaste comprises:

| | |
|---|---|
| Sorbitol (70% aq.) | 52.0 g |
| Sodium Saccharine | .3 g |
| Trisodium Phosphate | 1.1 g |
| Precipitated Silica | 20.0 g |
| Glycerine | 18.0 g |
| Sodium Flouride | .3 g |
| Water | 3.0 g |
| Sodium Alkyl Sulfate (28.8 aq.) | 4.0 g |
| Flavoring | 1.0 g |
| Active Ingredient | $.2-.2*10^{-8}$ mg |

An exemplary formulation of a mouthwash comprises:

| | |
|---|---|
| Water | 89.0 g |
| 1-methoxypropanol | 7.0 g |
| n-propanol | 1.0 g |
| Saccharine | .06 g |
| Glycerol | 1.3 g |
| Flavoring | 1.0 g |
| VPK-Ac-CC-Ac-KPV dimer (SEQ ID NO: 8) | $.1-.1*10^{-8}$ mg |

In another preferred embodiment of the invention these compositions are topically or systemically applied to treat a candida infection of the oral cavity. Topical administration may be made with manual application of creams or gels, gargling of mouthwash, brushing with toothpaste, chewing on tablets, holding lozenges in the mouth or with an atomized spray. Systemic administration may be made by ingestion of hard tablets, soft tablets or capsules. In yet another preferred embodiment of the invention these peptides are used in combination with a therapeutically effective amount of a fungicide selected from the group consisting of: itraconazole, econazole, ketoconazole, miconazole and fluconazole. In yet another preferred embodiment of the invention these peptides are used in combination with a therapeutically effective amount of a gram positive or gram negative antibiotics selected from the group consisting of: aminglycosides, amoxicillin, ampicillin, azithramycin, erythromycin, nafcillin, penecillin, quinupuristin dalfopristin and vancomycin.

The formulation of tablets are well known in the art. An exemplary formulation of a hard gelatinous tablet comprises:

| | |
|---|---|
| Gelatine Bloom 30 | 70.0 mg |
| Maltodextrin MD 05 | 108.0 mg |
| di-α-tocopherol | 2.0 mg |
| Sodium ascorbate | 10.0 mg |
| Microcrystalline cellulose | 48.0 mg |
| Magneisum stearate | 2.0 mg |
| Active Ingredient | $.2*10^{-4}-.2*10^{-11}$ mg |

An exemplary formulation of a hard tablet comprises:

| | |
|---|---|
| Annhydrous lactose | 130.5 mg |
| Microcrystalline cellulose | 80.0 mg |
| di-α-tocopherol | 2.0 mg |
| Sodium ascorbate | 10.0 mg |
| Polyvinylpyrrolidone K30 | 5.0 mg |
| Magnesium stearate | 2.0 mg |
| Active Ingredient | $.2*10^{-4}-.2*10^{-11}$ mg |

The following examples teach the utility of a-MSH as a fungicide in general and anti-candidal fungicide in particular. Methods in microbiology, molecular biology and biochemistry used but not explicitly described in this disclosure are amply described throughout the literature and well within the ability of one skilled in the art.

The peptides used in the following examples include: α-MSH (1–13) (SEQ. ID. NO. 4), (4–10) (SEQ. ID. NO: 2) (6–13) (SEQ. ID. NO: 3), and (11–13) (SEQ. ID. NO. 1), all of which were N-acetylated and C-amidated, and ACTH (1–39) (SEQ ID NO: 5) and (18–39) (SEQ ID NO: 6) (CLIP). These peptides were prepared by solid-phase peptide synthesis and purified by reversed phased high performance liquid chromatography. Some examples also include a dimer of the amino acid sequence KPV (SEQ. ID. NO. 1), VPK-Ac-CC-Ac-KPV (SEQ. ID. NO. 8), which also was N-acetylated and C-amidated (KPV dimer) (SEQ ID NO: 1). Dimers can be formed by adding cysteines at the N-termini of any of the above polypeptides and allowing the cysteines of two polypeptides to form a disulfide bond. Both homodimers and hetero-dimers can be formed using this method.

*C. albicans* (clinical isolate) was obtained from the collection of the Department of Microbiology, Ospedale Maggiore di Milano and maintained on Sabouraud's agar slants and periodically transferred to Sabouraud's agar plates and incubated for 48 hours at 28° C. To prepare a stationary growth phase yeast, a colony was taken from the agar plate and transferred into 30 ml Sabouraud-dextrose broth and incubated for 72 hours at 32° C. Cells were centrifuged and suspended in Hank's balanced salt solution ("HBSS") to the desired concentration. Viability, determined by the exclusion of 0.01% methylene blue, remained >98%.

Statistical significance disclosed in the examples below was analyzed using one-way analysis of variance and the Student's t test. Probability values greater than 0.05 were considered significant.

EXAMPLE 1

The first example suggests that α-MSH (11–13) (SEQ ID NO: 1), (6–13) (SEQ ID NO: 3) and (1–13) (SEQ ID NO:

4) exhibit similar anticandidal properties as flucanazole over an exceedingly broad range of concentrations.

*C. albicans* ($1 \times 10^6$/ml in HBSS) was incubated in the presence of absence or (1–13) (SEQ ID NO: 3) or (11–13) (SEQ ID NO: 1) at concentrations in the range of $10^{-15}$ M to $10^{-6}$ M for 2 hours at 37° C. Cells were then washed in cold distilled water and diluted with HBSS to a concentration of 100 organisms/ml. One-ml aliquots were dispensed on blood agar plates and incubated for 48 hours at 37° C. Organism viability was estimated from the number of colonies formed.

In subsequent experiments using familiar procedures we compared activity of α-MSH (4–10) (SEQ ID NO: 2), (6–13) (SEQ ID NO: 3), (11–13) (SEQ ID NO: 1), ACTH (SEQ ID NO: 5) (1–39), (18–39) (SEQ ID NO: 6) and fluconazole, the latter an established antifungal agent. Melanocortin peptides and fluconazole were tested in concentrations of $10^{-6}$ M to $10^{-4}$ M. There were at least six replicates for each concentration of peptide.

Figure 1:
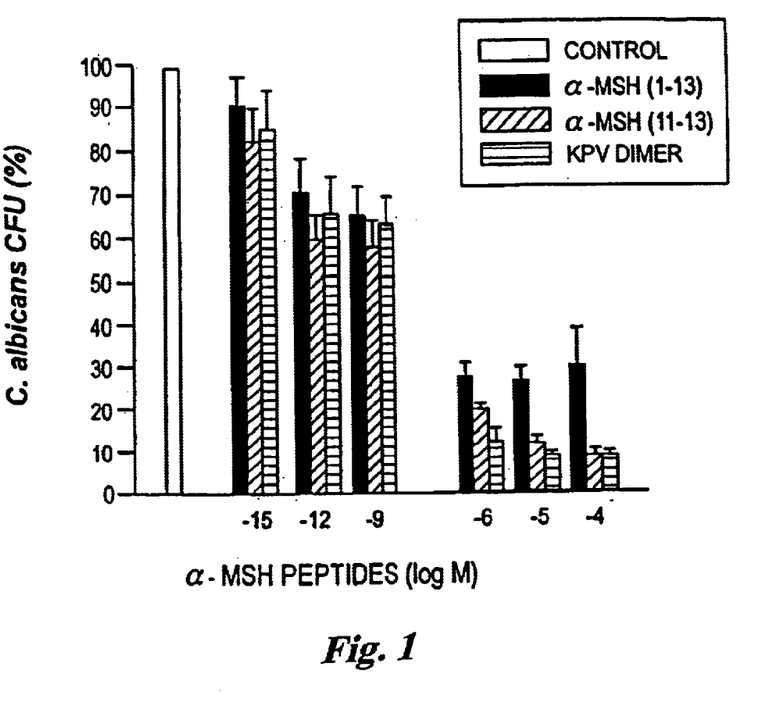
FIG. 1 illustrates the effect of α-MSH (1–13) (SEQ ID NO: 4) and (11–13) (SEQ ID NO: 1) and the peptide VPK-Ac-CC-Ac-KPV (SEQ ID NO: 8) on *C. albicans* colony forming units compared to controls. All three molecules significantly decreased *C. albicans* colony forming units over a broad range of peptide concentrations.

FIG. 1 shows that *C. albicans* colony forming units (CFU) were greatly reduced by α-MSH (1–13) (SEQ ID NO: 4) and (11–13) (SEQ ID NO: 1). FIG. 1 also shows that the VPK-Ac-CC-Ac-KPV (SEQ ID NO: 8) peptide also inhibited *C. albicans* colony formation). Concentrations of all three peptides from $10^{-12}$ M to $10^{-4}$ M had significant inhibitory effects on CFU (p<0.01 vs. control).

Figure 2:
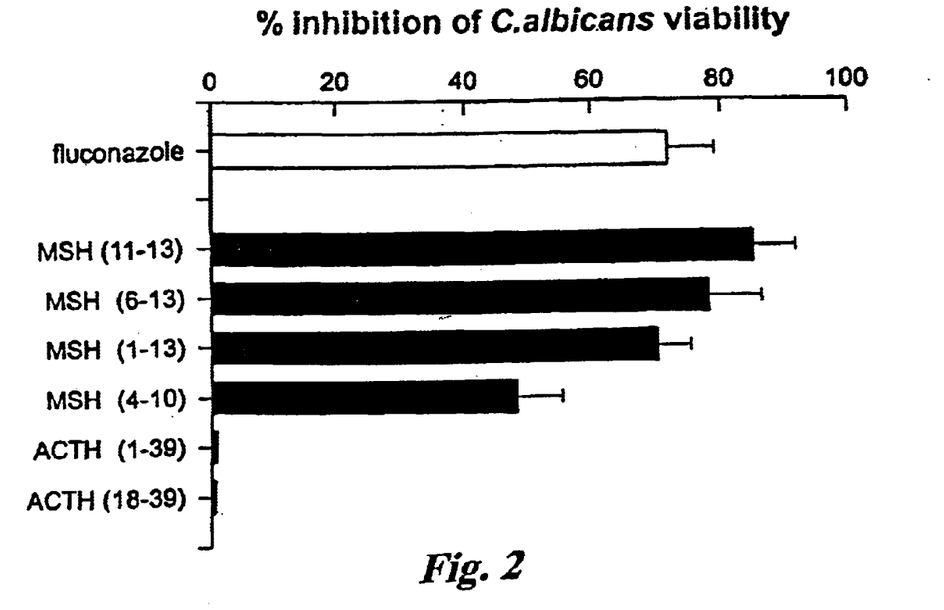
FIG. 2 (peptides shown in SEQ ID NOS 1, 3, 4, 2 5 and 6, respectively, in order of appearance) represents a comparison of candidacidal activity of certain melanocortin peptides and fluconazole (all $10^{-6}$ M). The most effective of the melanocortin peptides were those including the C-terminal amino acid sequence of α-MSH, namely, α-MSH (1–13) (SEQ ID NO: 4), (6–13) (SEQ ID NO:3) and (11–13) (SEQ ID NO: 1).
Figure 3A:
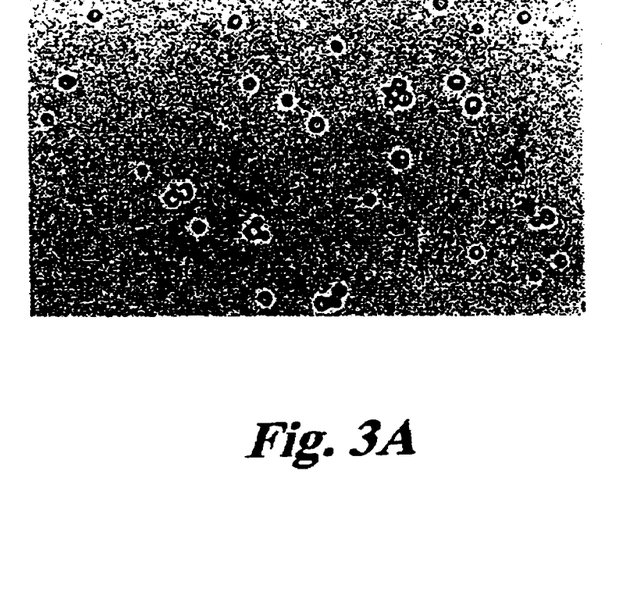
FIG. 3B shows a horse serum-induced germination of *C. albicans*.
FIG. 3C shows the effect of α-MSH (1–13) (SEQ ID NO: 4) treatment on germination of *C. albicans*
FIG. 3D shows the effect of α-MSH (11–13) (SEQ ID NO: 1) treatment on germination of *C. albicans*
Figure 3B:
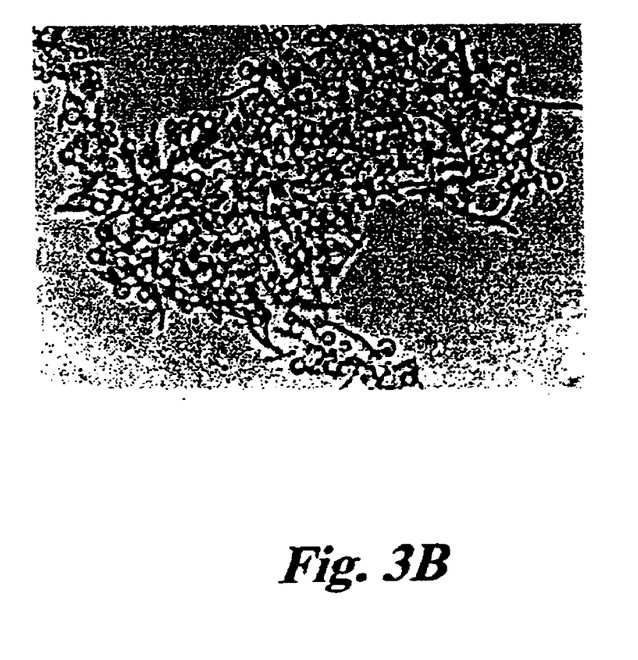
Figure 3C:
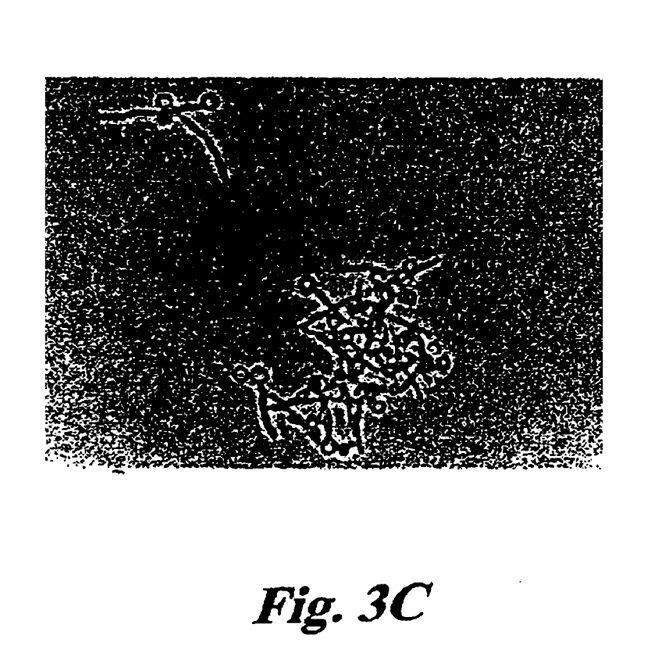
Figure 3D:
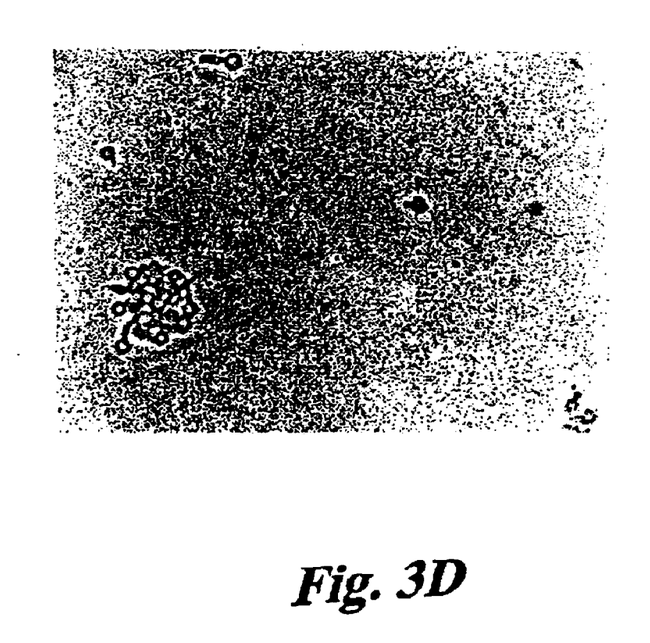

FIG. 2 demonstrates that in experiments comparing the relative potency of $10^{-4}$ M melanocortin peptides in reducing *C. albicans* viability, α-MSH (11–13) (SEQ ID NO: 1), (6–13) (SEQ ID NO: 3) and (1–13) (SEQ ID NO: 4) were the most effective. Their inhibitory activity was similar to that of equimolar fluconazole. The core α-MSH sequence (4–10) (SEQ ID NO: 2) which has behavioral effects but little anti-inflammatory activity, caused approximately 50% inhibition of CFU. FIG. 2 also shows that although this inhibitory effect was substantial (p<0.01 vs. control), it was significantly less than that caused by α-MSH fragments bearing the KPV (SEQ ID NO: 1) signal sequence, i.e., α-MSH (6–13) (SEQ ID NO: 3) and (11–13) (SEQ ID NO: 1) p<0.01), or the parent molecule α-MSH(1–13) (SEQ ID NO: 4) (p<0.05). ACTH (1–39) (SEQ ID NO: 5) and the ACTH fragment (18–39) (SEQ ID NO: 6) did not reduce *C. albicans* viability. Even higher concentrations of these ACTH peptides (up to $10^{-4}$ M) were likewise ineffective in reducing *C. albicans* CFU (results not shown in the figures).

These results show that α-MSH (1–13) (SEQ ID NO: 4), its C-terminal tripeptide (11–13) (SEQ ID NO: 1), and other α-MSH fragments have significant fungicidal effects against *C. albicans*. The most effective of the α-MSH peptides were those including the C-terminal amino acid sequence KPV (SEQ ID NO: 1) of the α-MSH sequence. i.e., α-MSH (1–13) (SEQ ID NO: 4), (6–13) (SEQ ID NO: 3) and (11–13) (SEQ ID NO: 1). In addition, the sequence VPK-Ac-CC-Ac-KPV (SEQ ID NO: 8) has also been shown to be at least as effective α-MSH (11–13) (SEQ ID NO: 1) against microbes. The α-MSH cores sequence (4–10) (SEQ ID NO: 2) which is known to influence learning and memory, but has little antipyretic and anti-inflammatory influence, was effective, but less so. The ACTH peptides (1–39) (SEQ ID NO: 5) and (18–39) (SEQ ID NO: 6) did not have significant candidacidal effects. These observations indicate that antifungal activity is not common to all melanocortin peptides, but rather that is specific to α-MSH amino acids sequences, and most particularly to the C-terminal amino-acid sequences of α-MSH. This strongly suggest that α-MSH (1–13) (SEQ ID NO: 4), its C-terminal tripeptide (11–13) (SEQ ID NO: 1), and other α-MSH fragments could server as a basis for a therapeutic treatment of acute and chronic candidal infections of the oral cavity or as antifungal agent against cadidal growth on denture surfaces.

EXAMPLE 2

Example 2 demonstrates that α-MSH (1–13) (SEQ ID NO: 4), (6–13) (SEQ ID NO: 3) or (11–13) (SEQ ID NO: 1) strongly inhibits Candidal germination. *C. albicans* from stationary phase cultures were washed twice with distilled water and suspended in HBSS to a final concentration of $2 \times 10^6$/ml. Hyphal growth was induced by addition of 10% inactivated horse serum (GIBCO/BRL, Great Britain) to yeast incubated for 45 minutes at 37° C. with continuous shaking. Horse serum was removed by washing cells twice with HBSS and incubation was continued for 60 minutes at 37° C. in the presence of α-MSH (1–13) (SEQ ID NO: 4), (6–13) (SEQ ID NO: 3) or (11–13) (SEQ ID NO: 1) at a concentration of $10^{-6}$ M with continuous shaking. The percentage of filamentous cells was evaluated under a light microscope with the aid of hemocytometer. Experiments were run in triplicate and at least 200 cells were scored. Photomicrophraphs were taken with a MC100 camera attached to an Axioskop Zeiss microscope.

FIGS. 3A–D show that coincubation of *C. albicans* with α-MSH (1–13) (SEQ ID NO: 4) or (11–13) (SEQ ID NO: 1) inhibited germ tube formation induced by horse serum, α-MSH (1–13) (SEQ ID NO: 4) caused 28–32% reduction in the number of filamentous cells; the tripeptide inhibited germination by 54–58%. The octapeptide α-MSH (6–13) (SEQ ID NO: 3) had similar activity (approximately 50% inhibition)(not shown).

The pathogenesis of *C. albicans* infection involves adhesion of yeast cells to epithelial cells, commonly found in the mucosal membranes of the ears, eyes, nose and throat and/or endothelial cells, followed by morphologic switching of the yeast cells from the ellipsoid blastospore to various filamentous forms: germ tubes, pseudohyphae and hyphae. Gow, N. A., *Germ Tube Growth of Candida Albicans, Curr. Topics Med. Mycol.* 8, 43–45 (1997). The results also show that in addition to direct candicidal properties, α-MSH(1–13) (SEQ ID NO: 4), its C-terminal tripeptide (11–13) (SEQ ID NO: 1), and other α-MSH fragments interfere with germination and adhesion of candida to the epithelium. This suggests that if the germination and adhesion of candida could be interfered with, the invasive forms of chronic candidiasis that innervate the epithelium could be treated with therapy based upon α-MSH(1–13) (SEQ ID NO: 4), its C-terminal tripeptide (11–13) (SEQ ID NO: 1), and other α-MSH fragments.

EXAMPLE 3

Example 3 illustrates that α-MSH and its derivatives exhibit their anti-candidal properties without compromising the ability of human neutrophils to independently combat Candida. Venous blood (20 ml) from health volunteers was anticoagulated with heparin. Neutrophils were isolated using dextran sedimentation and Ficoll-Hypaque (Sigma Chemical Co., St. Louis, Mich., USA) centrifugation. Erythrocytes were lysed via hypotonic shock. Neutrophils represented at least 97% of the cell suspension. Cell viability, estimated by trypan blue exclusion, was >98%. Neutrophils were suspended to a final concentration in HBSS.

*C. albicans* ($1 \times^6$) were opsonized with human AB serum in a shaking water bath for 30 minutes at 37° C. Organisms were then incubated with neutrophils in medium or in medium with α-MSH (1–13) (SEQ ID NO: 4) or α-MSH (11–13) (SEQ ID NO: 1) in concentrations of $10^{-15}$ M to $10^{-4}$ M in a shaking water bath for 2 hours at 37° C. After incubation, the culture tubes were placed on ice stop growth and extracellular organisms were washed twice with centrifugation at 1000×g at 4° C. A 2.5% sodium desoxycholoate solution was added to obtain a suspension of $10^{-6}$ cells/ml. Two 1/100 serial dilutions in HBSS were made to obtain a final suspension of 100 cells/ml. Aliquots of 1 ml were dispensed on blood agar plates and incubated for 48 hours at 37° C. Colony forming units (CFUs) were counted at the end of the incubation period. Experiments were run in triplicate and repeated using blood from 5 different donors.

Figure 4:
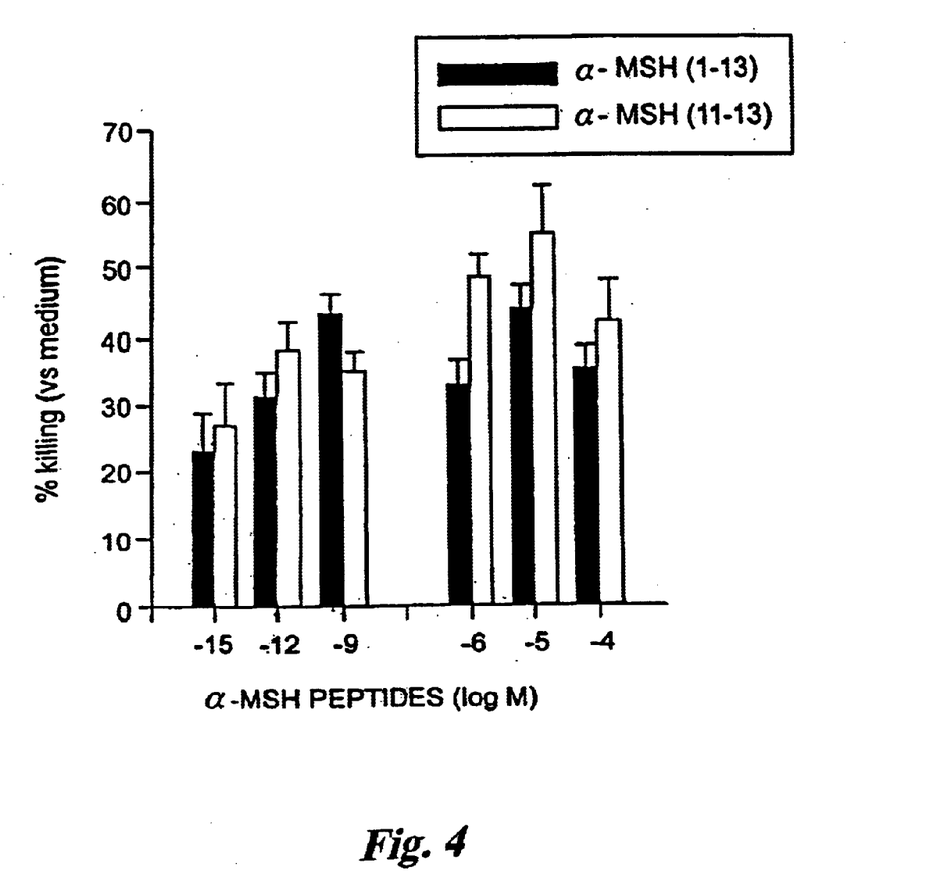
FIG. 4 illustrates the effect of α-MSH (1–13) (SEQ ID NO: 4) and (11–13) (SEQ ID NO: 1) on *C. albicans* killing by human neutrophils. Values are expressed as percent increase in killing vs. medium along. Scores are means±SEM.

FIG. 4 shows that α-MSH(1–13) (SEQ ID NO: 4) and (11–13) (SEQ ID NO: 1) enhanced the killing of *C. albicans* by human neutrophils when administered in concentrations of $10^{-12}$ M to $10^{-4}$ M (p<0.01). Therefore, enhanced killing occurred over a very broad range of concentrations including picomolar concentrations, i.e. the quantity of α-MSH found in human placenta. Catania, A., Airaghi, L., Garofalo, L., Cutuli, M., Lipton, J. M., *The Neuropeptide α-MSH in AIDS and Other Conditions in Humans*, Ann. N.Y Acad. Sci. 840, 848–856 (1998).

Reduced killing of pathogens is a dire consequence of therapy with corticosteroids and nonsteroidal anti-inflammatory drugs during infection. Stevens, D. L., *Could Nonsteroidal Anti-inflammatory Drugs (NSAIDS) Enhance Progression of Bacterial Infections to Toxic Shock Syndrome?*, Clin. Infect. Dis., 21, 977–80 (1997); Capsoni, F., Meroni, P. L., Zocchi, M. R.,Plebani, A. M., Vezio, M., *Effect of Corticosteroids on Neutrophil Function: Inhibition of Antibody-dependent Cell-mediated Cytotoxicity (ADCC)*, J Immunolpharmacol. 5 217–230 (1983). This effect is particularly dangerous in immunocompromised patients.

These results also suggest that α-MSH(1–13) (SEQ ID NO: 4), its C-terminal tripeptide (11–13) (SEQ ID NO: 1) and other α-MSH fragments would be useful for treatment of candidiasis in immunocompromised patients since these peptides appear not to reduce neutrophil chemotaxis and thus would not further comprise the immune system.

EXAMPLE 4

Example 4 suggests a cellular mechanism to explain how α-MSH exerts its anti-candidal properties. *C. albicans* ($10^{-6}$/ml), permeabilized with toluene/ethanol, were incubated at 37° C. with continuous shaking in the presence of $10^{-6}$ M α-MSH(1–13) (SEQ ID NO: 4), (11–13) (SEQ ID NO: 1), forskolin, an agent known to increase intracellular cAMP, or in medium alone. The reaction was stopped after 3 minutes by the addition of ice cold ethanol, cAMP was measured in duplicate using a commercial enzyme immunoassay (EIA) kit (Amersham, United Kingdom) after extraction via the liquid-phase method according to manufacturer's instructions. The effect of forskolin ($10^{-6}$ M) on *C. albicans* colony formation was determined using the same procedure as for α-MSH peptides.

Figure 5:
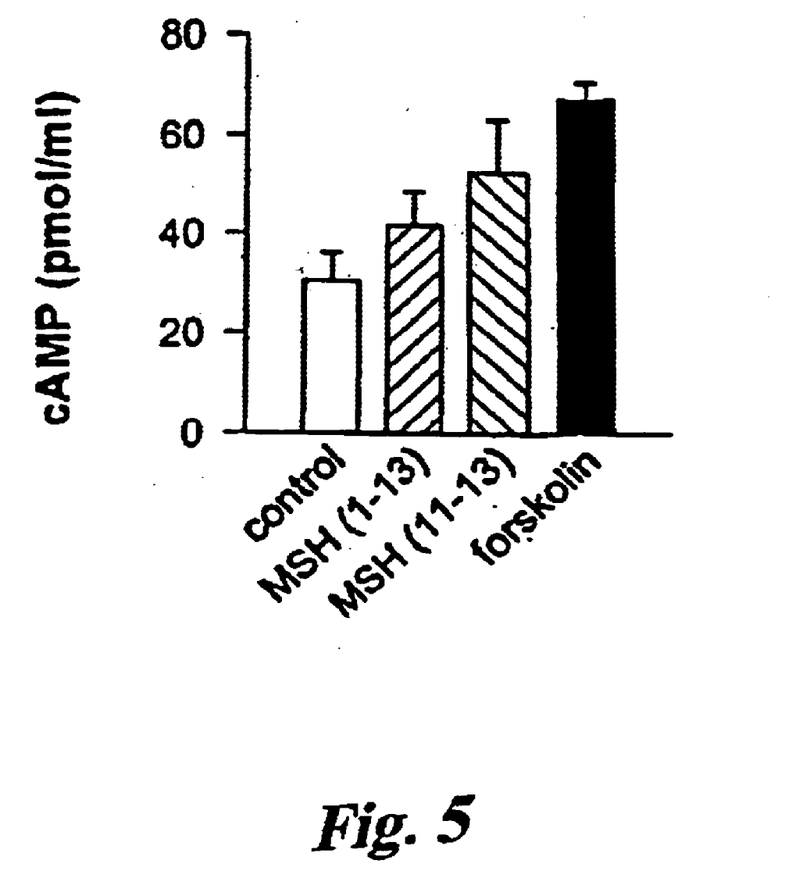
FIG. 5 illustrates the effect of α-MSH (1–13) (SEQ ID NO: 4), (11–13) (SEQ ID NO:1), and forskolin on cAMP content of *C. albicans*.
Figure 6:
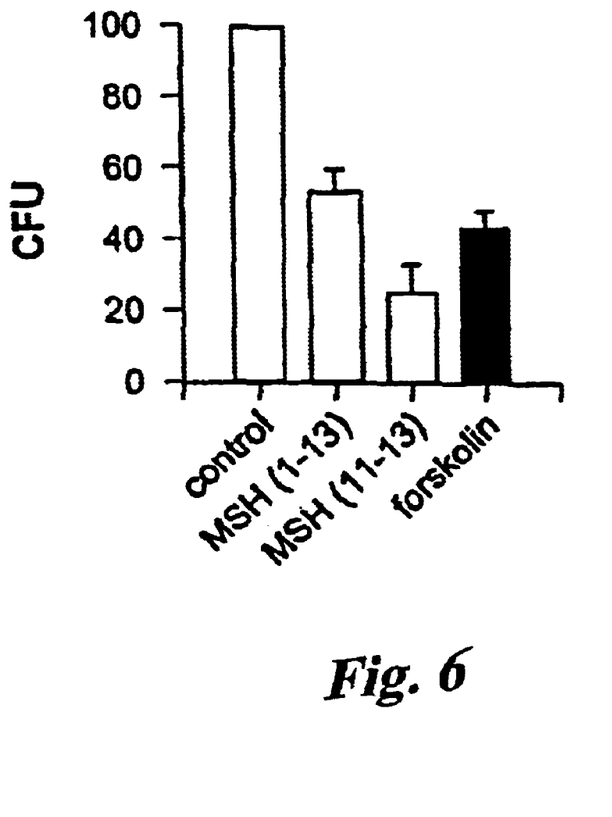
FIG. 6 illustrates the inhibitory effect of α-MSH (1–13) (SEQ ID NO: 4), (11–13) (SEQ ID NO: 1), and forskolin on *C. albicans* colony forming units.

Because many of the effects of α-MSH are known to be mediated by induction of cAMP, we measured effects of α-MSH peptides on cAMP accumulation in *C. albicans*. FIG. 5 shows that α-MSH (1–13) (SEQ ID NO: 4) and (11–13) (SEQ ID NO: 1) enhanced cAMP content in the yeast. FIG. 6 shows the increase was of the same order of magnitude as the induced by equimolar forskolin, an adenylate cyclase activator. To determine whether increases in cAMP could be responsible for reduction in CFU, we tested the effects of forskolin on *C. albicans* viability. Results showed that $10^{-6}$ M forskolin markedly inhibited *C. albicans* CFU relative to control (p<0.01). FIG. 6 demonstrates that the inhibitory effect was similar to that exerted by α-MSH.

The mechanism of action of natural antimicrobial agents is only partly understood. Most of these peptides, including the defensins, alter membrane permeability and impair internal homeostasis of the organism. The first contact is made between the cationic groups of the peptide and the negatively charged head of the target membrane. Then, the tertiary structure determines the mode of insertion of the peptide into membranes where they from ion channels or pores that disrupt cell integrity. It is known that cAMP-enhancing agents inhibit mRNA and protein synthesis in *C. albicans*. Bhattacharya, A., Datta, A., *Effect of Cyclic AMP on RMA and Protein Synthesis in C. albicans*, Biochem. Biophys. Res. Commun. 77: 1483–44 (1977).

In the present experiments it is shown that α-MSH induces cAMP accumulation in *C. albicans* and also that the cAMP-inducing agent forskolin inhibited colony formation. Without being limited by this theoretical explanation, it may be that the antimicrobial effect was caused by enhancement of this mediator.

EXAMPLE 5

Example 5 suggests functional equivalents to α-MSH and its derivatives. As used herein, a biological functional equivalent is defined as an amino acid sequence that is functionally equivalent in terms of biological activity.

Although the specific amino acid sequence described here are effective, it is clear to those familiar with the art that amino acids can be substituted in the amino acid sequence or deleted without altering the effectiveness of the peptides. Further, it is known that stabilization of a the α-MSH sequence can greatly increase the activity of the peptide and that substitution of amino acid D-forms for L-forms can improve or decrease the effectiveness of peptides. For example, a stable analog of α-MSH, [Nle$^4$,D-Phe$^7$]-α-MSH (SEQ ID NO: 10) which known to have marked biological activity on melanocytes and melanoma cells, is approximately 10 times more potent than the parent peptide in reducing fever. Holdeman, M., and Lipton, J. M.,*Antipyretic Activity of a Potent α-MSH Analog*, Peptides 6, 273–5 (1985). Further, adding amino acids to the C-terminal α-MSH (11–13) (SEQ ID NO: 1) sequence can reduce or enhance antipyretic potency. Deeter, L. B., Martin, L. W., Lipton, J. M., *Antipyretic Properties of Centrally Administered α-MSH Fragments in the Rabbit*, Peptides 9, 1285–8 (1989). Addition of glycine to form the 10–13 sequence slightly decreased the potency; the 9–13 sequence was almost devoid of activity, whereas the potency of the 8–13 sequence was greater than that of the 11–13 sequence. It is known that Ac-[D-K$^{11}$]-α-MSH 11–13-NH$_2$ (SEQ ID NO: 11) has the same general potency as the L-form of the tripeptide α-MSH 11–13 (SEQ ID NO: 1). Hiltz, M. E., Catania, A., Lipton, J. M., *Anti-inflammatory of α-MSH (11–13) (SEQ ID NO: 1) Analogs: Influences of Alterations in Stereochemistry*, Peptides 12, 767–71 (1991). However, substitution with D-proline in position 12 of the tripeptides rendered it inactive. Substitution with the D-form of valine position 13 or with the D-form of lysine at position 11 plus the D-form of valine at position 13 resulted in greater anti-inflammatory activity than with the L-form tripeptide. These examples indicate that alteration in the amino acid characteristics of the peptides can influence activity of the peptides or have little effect, depending upon the nature of the manipulation.

It is also believed that biological functional equivalents may be obtained by substitution of amino acids having similar hydropathic values. Thus, for example, isoleucine and leucine, which have a hydropathic index +4.5 and +3.8, respectively, can be substituted for valine, which has a hydropathic index of +4.2, and still obtain a protein having like biological activity. Alternatively, at the other end of the scale, lysine (−3.9) can be substituted for arginine (−4.5), and so on. In general, it is believed that amino acids can be successfully substituted where such amino acid has a hydropathic score of within about +/−1 hydropathic index units of the replaced amino acid.

EXAMPLE 6

An elderly diabetic patient presents with white plaque like lesions on the tongue. The patient has been a diabetic since childhood with a poor history of blood sugar control. Samples of the white keratinized lesions show moderate candidal fungal hyphae innervation. The patient is prescribed a pharmacologically effective amount of amphotericin and a pharmacologically effective concentration of α-MSH.

Examples 1–6 demonstrate the anti-candidal properties and uses of α-MSH and/or its derivatives. These are only illustrative and are not intended to limit the invention. It is understood that modifying the examples above does not depart from the spirit of the invention. It is further understood that the examples can be applied independently or in combination with each other.

What is claimed is:

1. A pharmaceutical composition for the treatment of oral candidiasis comprising a therapeutically effective amount of a peptide selected from the group consisting of KPV (SEQ. ID. NO. 1), VPK-Ac-CC-Ac-KPV (SEQ. ID. NO. 8) and HFRWGKPV (SEQ. ID. NO. 3) in combination with a therapeutically effective amount of a fungicide.

2. The composition of claim 1 wherein said fungicide is selected from the group consisting of: itraconazole, econazole, ketoconazole, miconazole and fluconazole.

3. The composition of claim 1 further comprising a therapeutically effective amount of an antibiotic.

4. The composition of claim 3 wherein said antibiotic further comprises a gram negative antibiotic.

5. The composition of claim 3 wherein said antibiotic further comprises a gram positive antibiotic.

6. The composition of claim 3 wherein said antibiotic is selected from the group consisting of: aminglycosides, amoxicillin, ampicillin, azithramycin, erythromycin, nafcillin, penicillin, quinupuristin dalfopristin and vancomycin.

7. The pharmaceutical composition of claim 1 further solvated in a carrier.

8. The composition of claim 1 wherein the concentration of said peptide is at least $10^{-12}$M.

9. The composition of claim 7 wherein the carrier is selected from the group consisting of: creams, gels, mouthwashes, toothpastes, tablets, and atomized sprays.

10. A pharmaceutical composition for the treatment of oral candidiasis comprising a therapeutically effective amount of a peptide selected from the group consisting of KPV (SEQ. ID. NO. 1), VPK-Ac-CC-Ac-KPV (SEQ. ID. NO. 8). and HFRWGKPV (SEQ. ID. NO. 3) in combination with a therapeutically effective amount of a fungicide and a therapeutically effective amount of an antibiotic.

11. The composition of claim 10 wherein said fungicide is selected from the group consisting of: itraconazole, econazole, ketoconazole, miconazole and fluconazole.

12. The composition of claim 1 wherein said antibiotic further comprises a gram positive antibiotic.

13. The composition of claim 10 wherein said antibiotic further comprises a gram negative antibiotic.

14. The composition of claim 10 wherein said antibiotic is selected from the group consisting of: aminglycosides, amoxicillin, ampicillin, azithramycin, erythromycin, nafcillin, penicillin, quinupuristin dalfopristin and vancomycin.

15. The pharmaceutical composition of claim 10 further solvated in a carrier.

16. The composition of claim 10 wherein the concentration of said peptide is at least $10^{-12}$M.

17. The composition of claim 15 wherein the carrier is selected from the group consisting of: creams, gels, mouthwashes, toothpastes, tablets, and atomized sprays.

18. The composition of claim 1 wherein the peptide is KPV (SEQ ID NO: 1).

19. The composition of claim 1 wherein the peptide is VPK-Ac-CC-Ac-KPV (SEQ ID NO: 8).

20. The composition of claim 1 wherein the peptide is HFRWGKPV (SEQ ID NO: 3).

21. The composition of claim 10 wherein the peptide is KPV (SEQ ID NO: 1).

22. The composition of claim 10 wherein the peptide is VPK-Ac-CC-Ac-KPV (SEQ ID NO: 8).

23. The composition of claim 10 wherein the peptide is HFRWGKPV (SEQ ID NO: 3).

* * * * *